United States Patent
Harder

(10) Patent No.: US 11,826,135 B2
(45) Date of Patent: Nov. 28, 2023

(54) METHOD AND SYSTEM FOR AUTOMATICALLY POSITIONING A REGION OF INTEREST OF A PATIENT FOR A MEDICAL IMAGING EXAMINATION

(71) Applicant: Siemens Healthcare GmbH, Erlangen (DE)

(72) Inventor: Martin Harder, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 248 days.

(21) Appl. No.: 17/032,559

(22) Filed: Sep. 25, 2020

(65) Prior Publication Data

US 2021/0093221 A1 Apr. 1, 2021

(30) Foreign Application Priority Data

Sep. 27, 2019 (DE) .......................... 102019214887.5

(51) Int. Cl.
*A61B 5/00* (2006.01)
*A61B 5/055* (2006.01)
(Continued)

(52) U.S. Cl.
CPC .............. *A61B 5/055* (2013.01); *A61B 90/39* (2016.02); *G06T 7/11* (2017.01);
(Continued)

(58) Field of Classification Search
CPC ................ A61B 5/055; A61B 2080/39; A61B 2080/3954; G06T 2207/10088;
(Continued)

(56) References Cited

U.S. PATENT DOCUMENTS

2013/0033700 A1* 2/2013 Hallil ................... A61N 5/1071
378/63
2016/0092078 A1 3/2016 Braun et al.
(Continued)

FOREIGN PATENT DOCUMENTS

DE 102014219667 B3 3/2016
DE 102014223103 A1 5/2016
(Continued)

OTHER PUBLICATIONS

German action dated Sep. 8, 2020, Application No. 10 2019 214887.5.

*Primary Examiner* — Joel F Brutus
(74) *Attorney, Agent, or Firm* — Banner & Witcoff Ltd.

(57) ABSTRACT

In a method and system for automatically positioning a region of interest of a patient for a medical imaging examination in an isocenter of a medical imaging apparatus, the region of interest of the patient is brought into a patient receiving region of the medical imaging examination for a position-determination measurement, a position-determination measurement is performed to capture position-determination image data, the position-determination image data is analyzed to determine a position of the region of interest of the patient from the position-determination image data, and the patient is automatically positioned such that the position of the region of interest of the patient coincides with the position of the isocenter of the medical imaging apparatus.

29 Claims, 3 Drawing Sheets

(51) Int. Cl.
*A61B 90/00* (2016.01)
*G06T 7/11* (2017.01)

(52) U.S. Cl.
CPC ............... *A61B 2090/3954* (2016.02); *G06T 2207/10088* (2013.01); *G06T 2207/20081* (2013.01); *G06T 2207/20084* (2013.01); *G06T 2207/20101* (2013.01); *G06T 2207/30004* (2013.01)

(58) Field of Classification Search
CPC . G06T 2207/20081; G06T 2207/20084; G06T 2207/20101; G06T 2207/30004
See application file for complete search history.

(56) References Cited

U.S. PATENT DOCUMENTS

| | | |
|---|---|---|
| 2016/0128666 A1 | 5/2016 | Grasruck et al. |
| 2018/0228450 A1 | 8/2018 | Vega et al. |
| 2019/0001155 A1* | 1/2019 | Ohishi ............... A61N 5/103 |
| 2019/0008411 A1 | 1/2019 | Faigle et al. |
| 2019/0057515 A1 | 2/2019 | Teixeira et al. |
| 2019/0220986 A1* | 7/2019 | Magro ............... A61B 6/032 |

FOREIGN PATENT DOCUMENTS

| | | | |
|---|---|---|---|
| EP | 3671641 A1 | 6/2020 | |
| WO | 2019120196 A1 | 6/2019 | |

\* cited by examiner

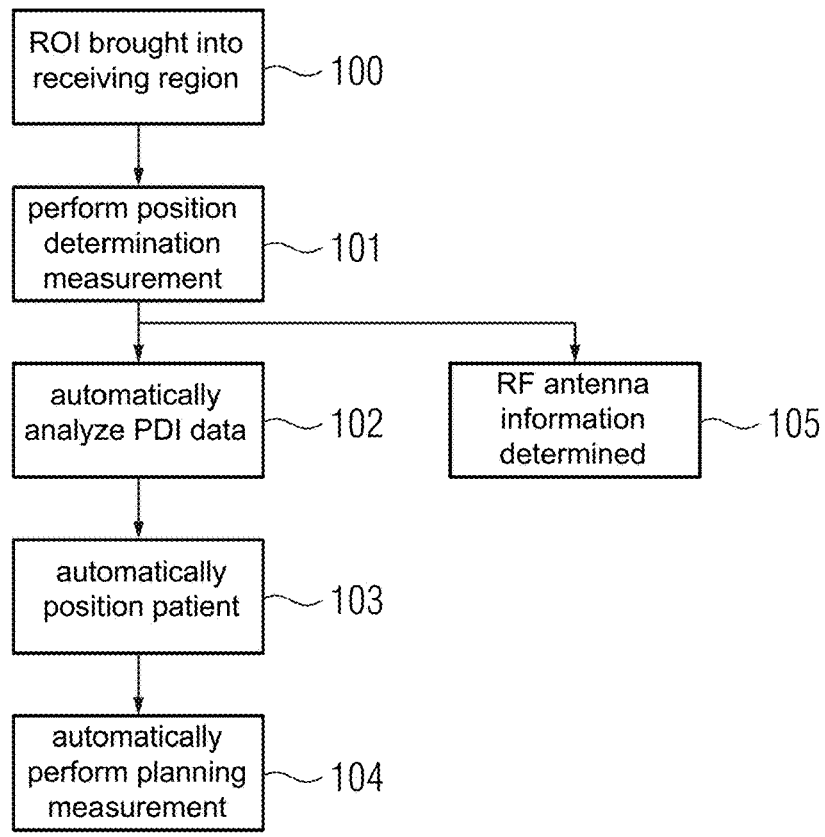
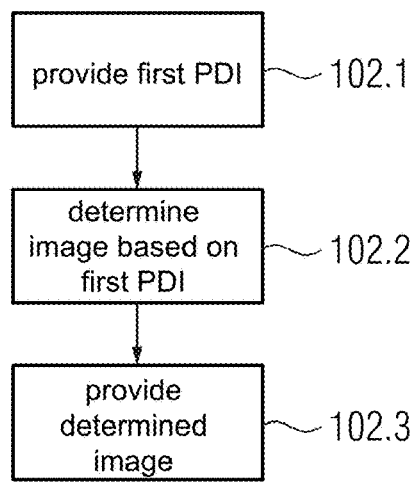

METHOD AND SYSTEM FOR AUTOMATICALLY POSITIONING A REGION OF INTEREST OF A PATIENT FOR A MEDICAL IMAGING EXAMINATION

CROSS REFERENCE TO RELATED APPLICATIONS

This patent application claims priority to German Patent Application No. 102019214887.5, filed Sep. 27, 2019, which is incorporated herein by reference in its entirety.

BACKGROUND

Field

The present disclosure relates to methods and systems for automatically positioning a region of interest of a patient for a medical imaging examination in an isocenter of a medical imaging apparatus. The disclosure is also based on a computer-implemented method for identifying a region of interest of a patient in a position-determination image, and on a provider system for providing a resultant image, which is determined according to the computer-implemented method for identifying a region of interest of a patient in a position-determination image. In addition, the present disclosure is based on a computer program product comprising a program for performing the method for automatically positioning a region of interest of a patient for a medical imaging examination, and an electronically readable data storage medium.

Related Art

For medical imaging examinations, in particular for magnetic resonance examinations, it is often important for planning the medical imaging examinations to perform a planning measurement first using the medical imaging apparatus. A user can then plan the medical imaging examination, in particular the magnetic resonance examination, on the basis of planning image data from the planning measurement. For instance, the user, in particular a medical operator, thereby specifies a slice positioning and/or a slice thickness etc. for individual measurements. In order to be able to perform slice planning in the planning image data, however, it is necessary to position the region of interest for the planning measurement exactly and/or correctly within the isocenter of the medical imaging apparatus, in particular of the magnetic resonance apparatus.

It is often difficult, however, for an inexperienced and/or inexpert medical operator to position the region of interest exactly and/or correctly within the isocenter of the magnetic resonance apparatus. Moreover, the region of interest of the patient can also depend on an anatomy of the patient; for instance a position of a lung of a patient on a patient table may depend on a size of the patient and/or a particular anatomical feature of the patient. This can again also make it harder for an inexperienced and/or inexpert medical operator to position the region of interest exactly and/or correctly within the isocenter of the magnetic resonance apparatus.

In order to position the region of interest of the patient correctly and/or exactly in the isocenter of a medical imaging apparatus, in particular of a magnetic resonance apparatus, several position measurements must often be carried out until the region of interest is arranged correctly and/or exactly in the isocenter. This requires a very large amount of time to be spent on a medical imaging examination on a patient, however, and hence also reduces a patient throughput.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 2 is a flowchart of a method for automatically positioning a region of interest of a patient for a medical imaging examination in an isocenter of a medical imaging apparatus according to an exemplary embodiment.

FIG. 3 is a flowchart of a method for identifying a region of interest of a patient in a position-determination image according to an exemplary embodiment.

Figure 1:
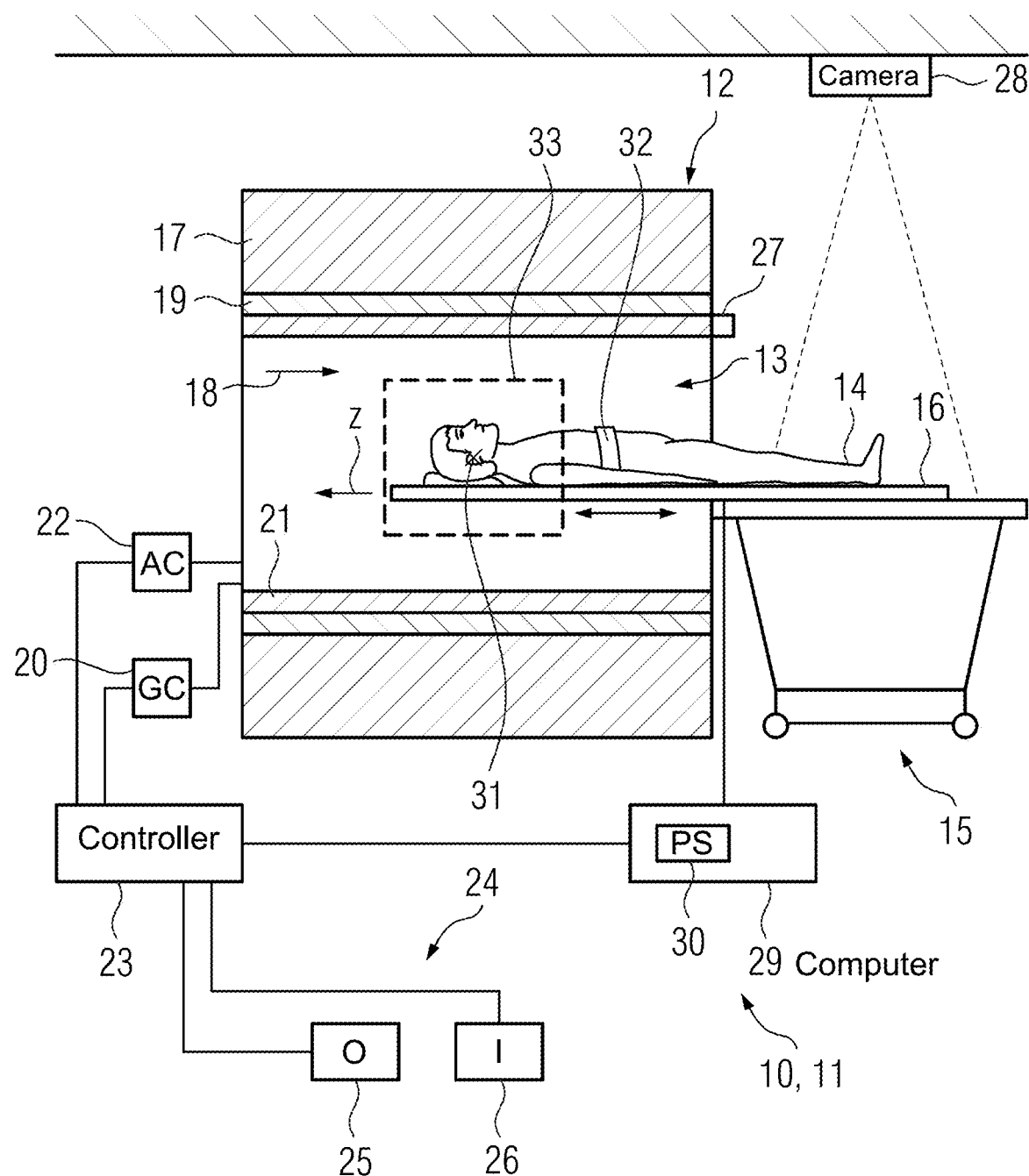
FIG. 1 shows a medical imaging apparatus according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to make it possible to position the region of interest easily and quickly in the isocenter of a medical imaging apparatus.

In an exemplary embodiment, a method for automatically positioning a region of interest of a patient for a medical imaging examination in an isocenter of a medical imaging apparatus comprises the following method steps:

bringing the region of interest of the patient into a patient receiving region of the medical imaging apparatus for a position-determination measurement;

performing the position-determination measurement and capturing position-determination image data;

analyzing the position-determination image data, wherein a position of the region of interest of the patient is determined from the position-determination image data; and automatically positioning the patient such that the position of the region of interest of the patient coincides with the position of the isocenter of the medical imaging apparatus.

In this context, an isocenter shall be understood to mean in particular a point and/or a region of the medical imaging apparatus that exhibits the most optimum and/or most ideal conditions for a medical imaging examination during operation of the medical imaging apparatus. The isocenter preferably describes a point inside an isocenter region. The isocenter is preferably situated within the patient receiving region. For example, the isocenter within a magnetic resonance apparatus, in particular within the patient receiving region, encompasses a point and/or a region at which the magnetic field of the magnetic resonance apparatus is designed to be the most homogeneous. For a magnetic resonance examination, the patient, in particular a region of interest of the patient, should be situated as exactly as possible in the isocenter. The isocenter for a medical imaging apparatus is preferably specified once at the time of installing the medical imaging apparatus.

The region of interest of the patient can comprise, for instance, an organ and/or an abnormality. A doctor is meant to provide a diagnosis relating to the region of interest of the patient by means of the medical imaging examination.

All medical imaging apparatuses that a person skilled in the art considers practical, for instance by a computed tomography apparatus and/or by a PET apparatus (positron emission tomography apparatus) may constitute the medical imaging apparatus. The medical imaging apparatus comprises particularly advantageously, however, a magnetic resonance apparatus, because in this case the long examination duration means that exact positioning of the patient, in particular of the region of interest of the patient, is particularly important in order to avoid repetitions of medical imaging examinations, in particular of a magnetic resonance examination.

The patient receiving region of the medical imaging apparatus is preferably configured to accommodate the patient, in particular the region of interest of the patient, during the medical imaging examination. For this purpose, the patient receiving region is surrounded at least partially by a scanner of the medical imaging apparatus. For example, the patient receiving region may be surrounded cylindrically by the scanner of the medical imaging apparatus. The isocenter is preferably arranged within the patient receiving region of the medical imaging apparatus.

For bringing the region of interest of the patient into the patient receiving region of the medical imaging apparatus, the patient is preferably already in position on a patient positioning apparatus of the medical imaging apparatus. For this purpose, the patient is preferably in a correct position for the forthcoming examination. For example, for a head examination the patient is in a "head-first" position, in which the head of the patient is moved first into the patient receiving region. For example, for a foot examination and/or a knee examination the patient is in a "feet-first" position, in which the feet of the patient are moved first into the patient receiving region. Before bringing the region of interest of the patient into the patient receiving region, all add-on units required, for instance an ECG unit and/or an infusion unit and/or a local radiofrequency antenna for a magnetic resonance examination, are preferably also already in position on the patient.

The region of interest of the patient is brought into the patient receiving region preferably by means of the patient positioning apparatus, in particular a movable patient table of the patient positioning apparatus. In addition, the region of interest of the patient can be brought into the patient receiving region by means of the patient table automatically and/or autonomously, in which case a computer controls the automatic and/or autonomous bringing of the region of interest of the patient into the patient receiving region. Moreover, bringing the region of interest of the patient into the patient receiving region can also be initiated by a user, for instance by a medical operator, by means of a user input at a user interface of the medical imaging apparatus. By bringing the region of interest of the patient into the patient receiving region for the position-determination measurement, the region of interest of the patient is positioned roughly within the patient receiving region. In this process, the region of interest of the patient need not coincide with the isocenter of the medical imaging apparatus. Instead it is sufficient for the position-determination measurement if the region of interest is arranged in a field of view (FOV) of the medical imaging apparatus, and is captured in the position-determination measurement.

The position-determination measurement is preferably used to determine a position of the region of interest of the patient within the patient receiving region, in particular with respect to the isocenter of the magnetic resonance apparatus. The position-determination measurement is performed by means of the medical imaging apparatus. A rapid measurement at a low resolution is preferably performed for said position-determination measurement, because this measurement is meant to be used merely for position determination. In particular here, a resolution of the position-determination measurement is lower than a resolution of a subsequent medical and/or diagnostic imaging measurement of the region of interest of the patient.

The position-determination measurement is preferably performed automatically and/or autonomously. The medical imaging apparatus is preferably controlled in this process by a computer, with the position-determination measurement performed automatically and/or autonomously. For example here, for the case in which the medical imaging apparatus is embodied as a magnetic resonance apparatus, the computer controls a radiofrequency antenna and a gradient coil suitably in order to beam the appropriate excitation pulses and/or spatial-encoding pulses into the patient receiving region, in particular into the FOV of the patient receiving region.

The position-determination image data is preferably likewise analyzed automatically and/or autonomously by the computer. For this purpose, the computer can also comprise an analyzer containing relevant analysis software and/or analysis programs, wherein the analysis of the position-determination image data is performed on execution of the relevant analysis software and/or the relevant analysis programs. The computer then determines automatically and/or autonomously from the position-determination image data the position of the region of interest of the patient within the patient receiving region. In this case, the computer preferably determines the position of the region of interest of the patient with respect to the position of the isocenter of the medical imaging apparatus. In particular, the computer determines a difference between the current position of the region of interest of the patient with respect to the position of the isocenter. It is then also possible to determine from the position of the region of interest of the patient with respect to the position of the isocenter of the medical imaging apparatus a change in position and/or a required positioning path for the region of interest of the patient in order to make the region of interest of the patient coincide with the isocenter of the medical imaging apparatus.

The patient is preferably positioned automatically and/or autonomously by the patient table of the patient positioning apparatus, with the computer of the medical imaging apparatus controlling the patient table. For example, the patient table of the patient positioning apparatus can thus be moved in a horizontal direction until the position of the region of interest coincides with the position of the isocenter.

Once the region of interest of the patient has reached the position of the isocenter, output information is preferably generated for the user, in particular for the medical operator, and output to the user via a user interface. The output information preferably comprises information to the user that the region of interest of the patient is in the correct position within the patient receiving region and is ready for a medical imaging examination. The computer of the medical imaging apparatus generates and/or outputs the output information preferably automatically and/or autonomously.

In an exemplary embodiment, the computer of the medical imaging apparatus comprises at least one processing module and/or a processor, wherein the computer is configured to perform the method according to the disclosure for automatically positioning a region of interest of a patient for a medical imaging examination in an isocenter of a medical imaging apparatus, and/or to perform individual method steps of the method according to the disclosure. Thus the computer is configured in particular to execute computer-readable instructions in order to perform the method according to the disclosure for automatically positioning a region of interest of a patient for a medical imaging examination in an isocenter of a medical imaging apparatus. The computer comprises in particular a memory unit, wherein computer-readable information is stored in the memory unit, wherein the computer is configured to load the computer-readable information from the memory unit and to execute the computer-readable information in order to perform the method according to the disclosure for automatically positioning a region of interest of a patient for a medical imaging examination in an isocenter of a medical imaging apparatus. The computer is thus configured to perform a method for automatically positioning a region of interest of a patient for a medical imaging examination in an isocenter of a medical imaging apparatus. In an exemplary embodiment, the computer includes processor circuitry that is configured to perform one or more operations and/or functions of the computer.

In an exemplary embodiment, one or more of the components of the computer can be embodied in the form of software components. In principle, however, some of these components can also be implemented in the form of software-aided hardware components, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software. Of course it is also conceivable that a plurality of the specified components are combined in the form of a single software component or software-aided hardware component.

By virtue of the disclosure, the region of interest of the patient can advantageously be positioned easily and quickly for a forthcoming medical imaging examination. In particular, the positioning process can thus be simplified for an inexperienced and/or inexpert medical operator and hence greater operating convenience provided in positioning the patient for a medical imaging examination. In addition, it is possible to reduce a total examination duration for a medical imaging examination and thus also to minimize a stress situation during the medical imaging examination for a patient.

Another advantage of the method according to the disclosure is that the position-determination data can also be used to determine a position of an add-on unit and/or to check whether an add-on unit is present. This can result in additional time being saved, because there is no need to perform further measurements, in particular separate measurements, for capturing add-on units. For example, it is thus possible to ascertain from the position-determination data a position and/or a presence of a local radiofrequency antenna for a magnetic resonance examination.

In an exemplary embodiment, the method to bring the region of interest of the patient into the patient receiving region comprises positioning the region of interest of the patient within an FOV (field of view) of the medical imaging apparatus. The field of view of the medical imaging apparatus preferably comprises a region and/or a field of vision of the medical imaging apparatus that exhibits the required physical conditions for an imaging. The FOV of the medical imaging apparatus is preferably located within the patient receiving region. For example, the FOV of a magnetic resonance apparatus encompasses a magnetic field that is as homogeneous as possible. Outside the FOV, and/or at edge regions of the FOV, the physical conditions may be different and/or may differ from the physical conditions in a center of the FOV. This embodiment of the disclosure makes it possible for a user, in particular a medical operator, to arrange and/or position the region of interest easily within the patient receiving region for the forthcoming position-determination measurement.

In an exemplary embodiment, it can be provided that a maximum FOV of the medical imaging apparatus is available for performing the position-determination measurement. A maximum FOV also encompasses edge regions of a capture region within the patient receiving region of the medical imaging apparatus, in which edge regions the physical image capture conditions are no longer ideal. Although this can lead to distortions in the captured image data, in particular in the position-determination image data, this is adequate for determining the position of the region of interest of the patient with respect to the isocenter of the medical imaging apparatus. Particularly advantageously, the maximum FOV encompasses a region that is at least 1.2 times larger than an FOV for a clinical and/or diagnostic imaging measurement. Particularly advantageously, the maximum FOV encompasses a region that is at least 1.3 times larger than an FOV for a clinical and/or diagnostic imaging measurement. Particularly advantageously, the maximum FOV encompasses a region that is at least 1.4 times larger than an FOV for a clinical and/or diagnostic imaging measurement. Particularly advantageously, the maximum FOV encompasses a region that is at least 1.5 times larger than an FOV for a clinical and/or diagnostic imaging measurement. Providing a maximum FOV for the position-determination measurement makes it possible for a user, in particular a medical operator, to arrange and/or position the region of interest easily within the patient receiving region.

In an exemplary embodiment, the region of interest of the patient is brought into the patient receiving region with the aid of a marking unit. The marking unit may comprise, for example, an optical marking unit, for instance an optical laser marking unit. The marking unit is preferably comprised by the medical imaging apparatus and arranged outside the patient receiving region. For example, the marking unit, in particular the optical laser marking unit, can project an optical marker, for instance a cross, on the patient. The patient, or the patient table, is thus preferably moved until a position of the region of interest of the patient coincides with a position of the projected marker, for instance with the projected cross. Since a distance of the marking unit from an FOV and/or isocenter of the medical imaging apparatus is predefined in the case of a permanently installed marking unit inside the medical imaging apparatus, it is thus possible for a medical operator to position the patient within the patient receiving region particularly easily. It can be provided here that the user, in particular the medical operator, needs to capture merely an approximate region of interest using the marking unit, and then the positioning within the FOV is performed automatically by means of the patient positioning apparatus, in particular by the patient table, under the control of the computer.

In an advantageous development of the method according to the disclosure, it can be provided that the region of interest of the patient is brought into the patient receiving region on the basis of registration data of the patient. The registration data of the patient is preferably saved and/or stored in the computer of the medical imaging apparatus and/or in a central registration computer, which is connected to the computer of the medical imaging apparatus. The patient registration data preferably comprises a name of the patient. The patient registration data can also comprise a weight of the patient. Alternatively or additionally, the patient registration data can also comprise a prior progression of a disease and/or a health condition of the patient. Alternatively or additionally, the patient registration data can also comprise an organ to be examined and/or a body region to be examined of the patient and/or a type of an examination by means of the medical imaging apparatus. Thus the region of interest of the patient can be brought into the patient receiving region particularly easily under the automatic control of the computer. In addition, it is thereby possible to minimize the time spent by a user, in particular the medical operator, during preparation and/or planning of the medical imaging examination on the patient.

In an advantageous development of the method according to the disclosure, it can be provided that the region of interest of the patient is brought into the patient receiving region on the basis of camera data from a camera. The camera preferably comprises a 3D camera which is configured to capture 3D camera data. In order to achieve an ideal and/or optimum view onto the patient, the camera, in particular the 3D camera, is preferably arranged on a ceiling of an examination room in which the medical imaging apparatus is situated. Alternatively or additionally, the camera, in particular the 3D camera, can also be arranged on the medical imaging apparatus and/or on a wall of the examination room. The camera data can be used advantageously to capture and/or determine an exact patient position with respect to the patient table and/or with respect to the isocenter of the medical imaging apparatus. In addition, the camera data can also be used to capture and/or determine an anatomy of the patient. This is done by first determining and/or finding an approximate region of interest of the patient in the camera data. The approximate region of interest of the patient is preferably determined and/or found from the camera data by means of the computer, which comprises for this purpose necessary analysis software and/or analysis programs. The approximate region of interest of the patient preferably encompasses a region of the patient that is larger than the region of interest of the patient but comprises the region of interest. For example, in the case that the region of interest of the patient takes the form of a lung region of the patient, the approximate region of interest of the patient encompasses the entire upper body of the patient. The approximate region of interest of the patient is subsequently brought into the patient receiving region preferably automatically and/or autonomously by means of the patient positioning apparatus under the control of the computer.

Thus bringing the region of interest of the patient into the patient receiving region can be performed according to the patient. In addition, it is possible to minimize the time spent by a user, in particular the medical operator, during preparation and/or planning of the medical imaging examination on the patient.

In an advantageous development of the method according to the disclosure, it can be provided that a surface image of the patient is found from the camera data of the camera, and a segmentation into individual regions is performed on the basis of the surface image of the patient. A 3D surface image for further processing, in particular segmentation, is found and/or determined preferably from 3D camera data from the 3D camera. The surface image of the patient preferably comprises an outline and/or a periphery of the patient. In addition, the surface image can also comprise depth information. The segmentation into individual regions preferably comprises rough segmentation into individual body regions and/or body segments of the patient. For example, the segmentation can comprise segmentation into the individual extremities, the head and the torso. The segmentation is preferably performed automatically and/or autonomously by the computer. For this purpose, the computer comprises appropriate software containing an analysis algorithm and/or comprises a segmentation algorithm in order to perform the segmentation into individual regions on the basis of the surface image of the patient.

This embodiment of the disclosure allows a segmented region which comprises the region of interest of the patient to be found in the camera data particularly quickly and preferably in an automated manner, and hence allows a position of the region of interest of the patient to be determined in an automated manner. In addition, it is possible to minimize manual errors and hence to reduce a total examination time on the patient.

In an advantageous development of the method according to the disclosure, it can be provided that the position-determination measurement takes at most 10 s to perform. Particularly advantageously, the position-determination measurement takes at most 8 s to perform. Particularly advantageously, the position-determination measurement takes at most 6 s to perform. Particularly advantageously, the position-determination measurement takes at most 5 s to perform. Particularly advantageously, the position-determination measurement takes at most 4 s to perform. Particularly advantageously, the position-determination measurement takes at most 3 s to perform. It is hence possible to provide a particularly rapid position-determination measurement for positioning the region of interest of the patient within the patient receiving region of the medical imaging apparatus and hence also to achieve particularly time-saving positioning of the patient, in particular of the region of interest of the patient, within the isocenter. In particular, a total examination time on the patient can thus also be reduced.

In an advantageous development of the method according to the disclosure, it can be provided that in the analysis of the position-determination image data, a position-determination image is created, and the region of interest of the patient is identified automatically in the position-determination image. Preferably, creating the position-determination image and identifying the region of interest of the patient in the position-determination image are performed automatically and/or autonomously by the computer. For the analysis of the position-determination image data, in particular identifying the region of interest within the position-determination image, additional examination data of the patient can also be included, for instance data such as information on which organs and/or body structures are comprised by the region of interest. By analyzing the position-determination image data, an exact position of the region of interest of the patient, for instance of an organ of the patient, is preferably determined and/or found in the z-direction of the medical imaging apparatus. In addition, a position of the region of interest of the patient can also be found in the y-direction and/or x-direction of the medical imaging apparatus. The z-direction of the medical imaging apparatus preferably comprises a direction of a longitudinal direction of the patient receiving region and/or an inward travel direction of the patient table.

In an advantageous development of the method according to the disclosure, it can be provided that the method comprises a computer-implemented method for identifying the region of interest of the patient in the position-determination image, comprising:

providing the position-determination image, wherein the position-determination image comprises the region of interest of the patient;

determining a resultant image by applying a trained function to input data comprising the position-determination image, wherein the resultant image comprises an identification of the region of interest;

providing the resultant image.

Providing the position-determination image and receiving the trained function take place in particular by means of an interface, in particular by means of an interface of a provider system. The resultant image dataset is determined in particular by means of a determination unit (determiner) and/or a computer, in particular by means of a determination unit and/or computer of the provider system. The provider system may be integrated inside the computer for performing the method for automatically positioning a region of interest of a patient for a medical imaging examination in an isocenter of a medical imaging apparatus. It is also possible for the provider system to be embodied separately from the computer, in which case the computer is preferably connected by means of a data transfer unit to the provider system for the purpose of data transfer. Said data transfer unit may include a wired and/or wireless data transfer unit.

Other terms for a trained function are trained mapping rule, mapping rule containing trained parameters, function containing trained parameters, algorithm based on artificial intelligence, and machine-learning algorithm. An example of a trained function is an artificial neural network, where the edge weights of the artificial neural network are equivalent to the parameters of the trained function. The term "neural net" can also be used instead of the term "neural network". In particular, a trained function may also be a deep artificial neural network (or a deep neural network). Another example of a trained function is a "support vector machine", and in particular other machine-learning algorithms may also be used as the trained function.

Thus identifying the region of interest within the position-determination image is based in particular on a machine learning method, also known as a deep learning method, which is based on the artificial neural network. An artificial neural network (ANN) is in particular a network of artificial neurons that is modeled in a computer program. The artificial neural network is typically based on an interconnection of a plurality of artificial neurons. The artificial neurons are typically arranged in different layers. Usually the artificial neural network comprises an input layer and an output layer, the neuron output of which is the only part of the artificial neural network to be visible. Layers lying between the input layer and the output layer are typically referred to as hidden layers. It is typical for an architecture and/or topology of an artificial neural network first to be initiated, and then to be trained in a training phase for a specific task or for a plurality of tasks in a training phase. Said training of the artificial neural network typically comprises changing a weight of a connection between two artificial neurons of the artificial neural network. The training of the artificial neural network can also comprise developing new connections between artificial neurons, removing existing connections between artificial neurons, adjusting threshold values of the artificial neurons and/or adding or removing artificial neurons.

The artificial neural network in particular has already been trained in advance suitably for identifying the region of interest of the patient in a position-determination image. For said training of the artificial neural network, in particular training image datasets are used in which a region of interest of the patient examination is already associated with examination information and/or anatomy information of the patient, for example. The medical training datasets are acquired in this case typically from training people and/or training patients who are different from the patient.

A trained function maps input data onto output data. Said output data may depend in particular also on one or more parameters of the trained function. The one or more parameters of the trained function can be determined and/or adjusted by training. Determining and/or adjusting the one or more parameters of the trained function can be based in particular on a pair composed of training input data and associated training output data, wherein the trained function for generating training output data is applied to the training input data. In general, a trainable function, i.e. a function containing one or more parameters yet to be adjusted, is also referred to as a trained function.

The trained function comprises at least one parameter, where the output values of the trained function depend on the value(s) of the at least one parameter. A parameter of the trained function is based in particular on the at least one training image dataset when the parameter of the trained function has been modified and/or adjusted in order to optimize a cost function based on the at least one training image dataset. This includes the case in which a plurality of, or all, parameters of the trained function have been modified and/or adjusted in order to optimize a cost function based on the at least one training image dataset.

The training dataset, in particular the training data, can comprise in particular patient examination information and/or patient anatomy information about the region of interest. The at least one training dataset can comprise training data that comprises an identification of the region of interest of the patient on the basis of the examination information and/or the anatomy information by means of shape recognition of body regions, for instance shape recognition of organs and/or bones and/or bone junctions such as, for example, a joint cavity, etc. Alternatively or additionally, the at least one training dataset can comprise training data that comprises an identification of the region of interest of the patient on the basis of the examination information and/or the anatomy information by means of recognizing landmarks. In this regard, a landmark shall be understood to mean in particular a distinctive structure and/or a distinctive region in the image data, which region is characteristic of an organ structure and/or a body region. Alternatively or additionally, the at least one training dataset can comprise training data that comprises an identification of the region of interest of the patient on the basis of the examination information and/or the anatomy information by means of segmentation into individual regions.

The resultant image comprises the identification of the region of interest of the patient in the position-determination image. By identifying the region of interest, the region of interest is localized in the resultant image, in other words a position of the region of interest in the resultant image is specified. The resultant image can comprise the position-determination image in which the region of interest is identified, in particular localized. In this case, the region of interest can be indicated in the resultant image.

Providing the resultant image preferably comprises providing the resultant image, in particular providing the identified and/or localized region of interest of the patient for positioning the patient, by means of the provider system. The resultant image can be provided in this case within the computer of the medical imaging apparatus.

This embodiment of the disclosure allows rapid identification of the region of interest of the patient in the position-determination image. In particular, an inexperienced and/or inexpert user, in particular an inexperienced and/or inexpert medical operator, can thereby be assisted advantageously in identifying the region of interest of the patient, while manual errors can advantageously be reduced and/or avoided.

In an advantageous development of the method according to the disclosure, it can be provided that the automatic positioning of the region of interest of the patient comprises moving a patient table automatically. The automatic movement of the patient table is controlled preferably by the computer of the medical imaging apparatus. The automatic movement of the patient table is only performed, however, if it is found in the analysis of the position-determination image data that a position of the region of interest of the patient does not coincide with the position of the isocenter of the medical imaging apparatus. The region of interest of the patient can thereby be positioned easily and quickly in the isocenter of the medical imaging apparatus. In particular, it is hence also possible to prevent advantageously manual errors in positioning the region of interest of the patient in the isocenter of the medical imaging apparatus. In addition, it may also be the case that it is not possible to recognize and/or determine the region of interest of the patient in the position-determination image data, for instance because the region of interest of the patient does not lie in the capture region of the medical imaging apparatus for a position-determination measurement and hence is not captured in the position-determination measurement. Again in this case, automatically moving the patient table, and thereby correcting a position of the region of interest of the patient, can cause the region of interest of the patient to enter the capture region for a fresh position-determination measurement. The automatic movement of the patient table preferably comprises moving the patient table by a maximum of ±25 cm. The automatic movement of the patient table preferably comprises moving the patient table by a maximum of ±22 cm. The automatic movement of the patient table preferably comprises moving the patient table by a maximum of ±18 cm. The automatic movement of the patient table preferably comprises moving the patient table by a maximum of ±15 cm.

In an advantageous development of the method according to the disclosure, it can be provided that the medical imaging examination comprises a magnetic resonance examination, and information on a radiofrequency antenna for the planned magnetic resonance examination is determined from the position-determination image data. The radiofrequency antenna preferably comprises a local radiofrequency antenna, which is arranged around the region of interest of the patient in order to capture magnetic resonance signals. In addition to positioning the region of interest of the patient within the patient receiving region, it is thereby also possible to check and/or verify the radiofrequency antenna being used and hence assist the medical operator in preparing the patient. In addition, information about a position of the region of interest can also be obtained from the position of the local radiofrequency antenna.

In an alternative embodiment of the disclosure, the information on the radiofrequency antenna to be used for the forthcoming magnetic resonance measurement can also be captured by means of a camera.

In an advantageous development of the method according to the disclosure, it can be provided that the captured information on the radiofrequency antenna includes a type of the radiofrequency antenna and/or a position of the radiofrequency antenna and/or an orientation of the radiofrequency antenna. On the basis of the captured information on the radiofrequency antenna, the computer can advantageously check and/or monitor automatically and/or autonomously whether the radiofrequency antenna being used is suitable for the forthcoming magnetic resonance examination. In addition, the computer can likewise use the captured information on the radiofrequency antenna to check and/or monitor automatically and/or autonomously a correct arrangement, in particular a position and/or orientation, of the radiofrequency antenna on the patient. It is thus advantageously possible at least to reduce and/or to prevent incorrect positioning of local radiofrequency antennas, and hence also to minimize a preparation time for preparing the patient for the medical imaging examination.

In an advantageous development of the method according to the disclosure, it can be provided that the captured information on the radiofrequency antenna is compared with examination information and/or patient registration information and/or a reference position for the radiofrequency antenna. The computer of the medical imaging apparatus preferably performs the comparison of the captured information on the radiofrequency antenna with examination information and/or patient registration information and/or a reference position for the radiofrequency antenna. Information on a region of interest of the patient and hence also a reference position for the radiofrequency antenna for the forthcoming magnetic resonance examination on the patient can be obtained from the examination information and/or the patient registration information. A deviation of a current position of the radiofrequency antenna from a reference position of the radiofrequency antenna can thus be determined particularly easily and quickly in an automated manner.

In an advantageous development of the method according to the disclosure, it can be provided that output information is generated as a function of the comparison of the captured information on the radiofrequency antenna with the examination information and/or the patient registration information and/or the reference position of the radiofrequency antenna, and is output. The output information is preferably generated and output for a user, in particular a medical operator. The output information is preferably generated automatically by the computer. The output information is preferably output automatically by means of a user interface of the medical imaging apparatus. A user, in particular a medical operator, can thereby be notified directly of incorrect positioning of the local radiofrequency antenna. Moreover, it may also be the case that, in addition to the output information to the user, a user input is needed for the examination procedure to continue. For example, the user can also be prompted by the output information to perform a suitable correction to a position of the local radiofrequency antenna. In addition, it may also be the case that after a correction to a position of the local radiofrequency antenna, a confirmation input can be input by the user at a user interface of the medical imaging apparatus, in particular of the magnetic resonance apparatus, to confirm the correction to the position of the local radiofrequency antenna.

In an advantageous development of the method according to the disclosure, it can be provided that after the automatic positioning of the patient, in particular of the region of interest of the patient, a planning measurement is performed for planning the medical imaging examination on the region of interest of the patient. The planning measurement is preferably used to capture in particular planning image data of the patient and to provide the user, in particular the medical operator, and/or a planning processor, with at least one planning image of the region of interest of the patient for planning the imaging examination, for instance a magnetic resonance examination. The user, in particular the medical operator, and/or a planning processor can use the at least one planning image to plan the medical imaging examination on the patient. By virtue of this embodiment of the disclosure, the forthcoming medical imaging examination on the region of interest of the patient can advantageously be planned easily and quickly. In particular, a user, in particular the medical operator, and/or a planning processor can thus use the at least one planning image to set and/or specify individual examination parameters for the forthcoming medical imaging examination. For example, a user, in particular the medical operator, and/or a planning processor can thus use the at least one planning image to determine and/or set for a magnetic resonance examination a slice thickness and/or a slice position and/or an orientation of a slice and/or a number of slices to be acquired, etc. In addition, it is hence possible to perform a rapid planning measurement, because the region of interest of the patient is already in the optimum position within the patient receiving region, in particular within the isocenter, for said planning measurement.

In an advantageous development of the method according to the disclosure, it can be provided that at least one planning image is generated and/or created from the planning measurement data of the planning measurement, wherein the at least one planning image comprises a magnified representation of the region of interest. In particular, a detailed view of the region of interest can be provided in the at least one planning image by providing a magnified representation of a segment of the region of interest of the patient. In particular, the region of interest can thus be presented in a zoom-view in the at least one planning image. This can in particular make easy planning possible for a user, in particular a medical operator, and/or a planning processor.

In an advantageous development of the method according to the disclosure, it can be provided that while the planning image is being provided and/or while the medical imaging examination is being planned, at least one adjustment measurement is performed for the forthcoming medical imaging examination. It is thereby advantageously possible to use a planning time, in particular a time that the medical operator and/or a planning processor needs to plan the medical imaging examination, for forthcoming adjustment measurements, and hence also advantageously to reduce a total examination time, in particular a time in which the patient is in position on the patient positioning apparatus and/or in which the patient occupies the medical imaging apparatus. In addition, it is thus also possible to perform adjustment measurements, which are conventionally performed back at the stage of positioning the patient in the patient receiving region, in particular in the isocenter of the medical imaging apparatus, only once the patient, in particular the region of interest of the patient, is positioned in the isocenter, and thereby also to reduce a preparation time for the medical imaging examination. The at least one adjustment measurement is preferably performed automatically and/or autonomously by the computer of the medical imaging apparatus while the planning image is being provided and/or while the medical imaging examination is being planned.

In an advantageous development of the method according to the disclosure, it can be provided that after performing the planning of the medical imaging examination, planning data is checked automatically, and output information is generated and provided on the basis of the check. The planning data is preferably checked automatically and/or autonomously by the computer of the medical imaging apparatus. In addition, the output information is generated and provided automatically and/or autonomously by the computer of the medical imaging apparatus. The planning of the medical imaging examination is preferably checked with regard to plausibility of the planning data. This embodiment has the advantage that feedback for the user, in particular the medical operator, about the set planning data is provided and output to the user immediately after the planning of the medical imaging examination. The output information is preferably output by means of an output unit of the medical imaging apparatus. Said output information can comprise visual output information and/or audible output information. Preferably, once planning of the medical imaging examination on the basis of the planning image is complete, the medical imaging examination is carried out on the region of interest of the patient.

The disclosure also relates to a computer-implemented method for identifying a region of interest of a patient in a position-determination image, comprising:
  providing the position-determination image, wherein the position-determination image comprises the region of interest of the patient;
  determining a resultant image by applying a trained function to input data comprising the position-determination image, wherein the resultant image comprises an identification of the region of interest;
  providing the resultant image.

The position-determination image preferably comprises position-determination image data from a position-determination measurement, wherein the position-determination measurement is performed by a medical imaging apparatus, and is provided by a provider system for determining a resultant image by applying a trained function to input data comprising the position-determination image.

This can facilitate rapid identification of the region of interest of the patient in the position-determination image. In particular, a robust and reliable method for identifying the region of interest of a patient in a position-determination image can thus be provided. In addition, an inexperienced and/or inexpert user, in particular an inexperienced and/or inexpert medical operator, can also be assisted advantageously in identifying the region of interest. It is also advantageously possible to reduce and/or prevent in particular manual errors in identifying the region of interest of the patient and/or in positioning the region of interest in the isocenter of the medical imaging apparatus.

In an advantageous development of the method according to the disclosure, it can be provided that the trained function is based on at least one training image dataset containing training data, wherein the training data comprises a position-determination image comprising examination information and/or anatomy information and comprising an associated region of interest.

The examination information and/or anatomy information may comprise, for example, the desired region of interest of the patient and/or information about an illness such as headaches, for instance, which indicate a region of interest of the patient. The trained function determines from the input data, in particular from the position-determination image, and from the examination information and/or the anatomy information a probable region of interest of the patient within the position-determination image. Then, in the training phase, the probable region of interest of the patient is compared with the region of interest of the patient. If there are differences and/or discrepancies between the probable region of interest of the patient and the region of interest of the patient, the trained function is adjusted on the basis of the difference and/or discrepancy between the probable region of interest of the patient and the region of interest of the patient. Thus different training image datasets may also form the basis for different body regions of interest of patients. In this case, a dedicated training image dataset containing training image data for a particular body region of interest of patients can be used.

By virtue of this embodiment of the disclosure, a trained function for rapid identification of a region of interest of a patient in a position-determination image can advantageously be provided. It is thereby possible in particular also to minimize a preparation time for preparing a magnetic resonance examination on a patient, because the rapid identification of the region of interest of the patient in the position-determination image can also provide easy and rapid positioning of the region of interest within an isocenter of the medical imaging apparatus, for instance of a magnetic resonance apparatus.

In an advantageous development of the method according to the disclosure, it can be provided that the trained function is based on at least one training image dataset containing training data, wherein the training data comprises a position-determination image comprising a characteristic shape of the region of interest, which characteristic shape is associated with the region of interest. For instance, if the region of interest comprises an organ, the associated characteristic shape can comprise the shape of the organ, for instance a shape of a liver and/or a shape of a heart. In addition, the associated characteristic shape can include also a shape of a bone and/or a shape of a joint and/or a shape of blood vessels etc. lying within the region of interest.

By virtue of this embodiment of the disclosure, a trained function for rapid identification of a region of interest of a patient in a position-determination image can advantageously be provided. It is thereby possible in particular also to minimize a preparation time for preparing a magnetic resonance examination on a patient, because the rapid identification of the region of interest of the patient in the position-determination image can also provide easy and rapid positioning of the region of interest within an isocenter of the medical imaging apparatus, for instance of a magnetic resonance apparatus.

In an advantageous development of the method according to the disclosure, it can be provided that the trained function is based on at least one training image dataset containing training data, wherein the training data comprises a position-determination image comprising landmark recognition in the region of interest, which landmark recognition is associated with the region of interest. Landmarks preferably include typical points and/or characteristic axes in an image that can be associated exactly with a specific organ and/or a specific joint and/or a specific body region.

By virtue of this embodiment of the disclosure, a trained function for rapid identification of a region of interest of a patient in a position-determination image can advantageously be provided. It is thereby possible in particular also to minimize a preparation time for preparing a magnetic resonance examination on a patient, because the rapid identification of the region of interest of the patient in the position-determination image can also provide easy and rapid positioning of the region of interest within an isocenter of the medical imaging apparatus, for instance of a magnetic resonance apparatus.

In an advantageous development of the method according to the disclosure, it can be provided that the trained function is based on at least one training image dataset containing training data, wherein the training data comprises a position-determination image comprising segmentation into organ structures and/or body structures of the region of interest, which segmentation is associated with the region of interest.

By virtue of this embodiment of the disclosure, a trained function for rapid identification of a region of interest of a patient in a position-determination image can advantageously be provided. It is thereby possible in particular also to minimize a preparation time for preparing a magnetic resonance examination on a patient, because the rapid identification of the region of interest of the patient in the position-determination image can also provide easy and rapid positioning of the region of interest within an isocenter of the medical imaging apparatus, for instance of a magnetic resonance apparatus.

In an advantageous development of the method according to the disclosure, it can be provided that the position-determination image comprises a 2D position-determination image, and the training data of the at least one training image dataset of the trained function comprises 2D training data. Using 2D images can provide particularly rapid identification of a region of interest of a patient in a position-determination image.

The disclosure is also based on a provider system for providing a resultant image, comprising an interface and a computer,
   wherein the interface and/or the computer are configured to provide the position-determination image,
   wherein the computer is configured to determine a resultant image by applying a trained function to input data comprising the position-determination image, wherein the resultant image comprises an identification of the region of interest, and
   wherein the interface is also configured to provide the resultant image.

Said provider system can be configured in particular to perform the above-described method according to the disclosure for identifying a region of interest of a patient in a position-determination image. The provider system is configured to perform this method and aspects thereof by the interface and the computer being configured to perform the relevant method steps.

The disclosure is also based on a medical imaging apparatus comprising a scanner, a patient receiving region, which is surrounded at least partially by the scanner, a patient positioning apparatus comprising a patient table, which can move in a horizontal direction, and a computer, wherein the medical imaging apparatus is configured to perform an above-described method for automatically positioning a region of interest of a patient for a medical imaging examination in an isocenter of a medical imaging apparatus.

The region of interest of the patient can advantageously be positioned easily and quickly for a forthcoming medical imaging examination by means of the medical imaging apparatus according to the disclosure. In particular, the positioning process can thus be simplified for an inexperienced and/or inexpert medical operator and hence greater operating convenience can be provided for positioning the patient. In addition, it is possible to reduce a total examination duration for a medical imaging examination and thus also to minimize a stress situation during the medical imaging examination for a patient.

The advantages of the medical imaging apparatus according to the disclosure are essentially the same as the advantages detailed above of the method according to the disclosure for automatically positioning a region of interest of a patient for a medical imaging examination in an isocenter of a medical imaging apparatus. Features, advantages or alternative embodiments mentioned in this connection can be applied likewise to the other subject matter, and vice versa.

Another aspect of the disclosure can be a medical imaging apparatus comprising a scanner, a patient receiving region, which is surrounded at least partially by the scanner, a patient positioning apparatus comprising a patient table, which can move in a horizontal direction, and a provider system, wherein the provider system is configured to perform an above-described computer-implemented method for identifying a region of interest of a patient in a position-determination image.

The disclosure is also based on a computer program product which comprises a program and can be loaded directly in a memory of a programmable computer, and comprises program means for performing a method for automatically positioning a region of interest of a patient for a medical imaging examination in an isocenter of a medical imaging apparatus when the program is executed in the computer.

The disclosure can also comprise a computer program product which comprises a program and can be loaded directly in a memory of a programmable computer, and which comprises program means for performing a method for identifying a region of interest of a patient in a position-determination image when the program is executed in the computer. The computer program product for performing the method for identifying a region of interest of a patient in a position-determination image may be part of the computer program product for performing the method for automatically positioning a region of interest of a patient for a medical imaging examination in an isocenter of a medical imaging apparatus, or else may comprise a separate computer program product.

In addition, the individual computer programs may require program means, e.g. libraries and auxiliary functions, for implementing the relevant embodiments of the methods according to the disclosure. Said individual computer programs can comprise software containing a source code, which still needs to be compiled and linked or just needs to be interpreted, or an executable software code, which for execution only needs to be loaded into a suitable computer.

The individual computer program products according to the disclosure can be loaded directly into a memory of a programmable computer, and comprise program code means in order to perform one of the methods according to the disclosure when one of the computer program products is executed in the computer. The computer program products may each be a computer program or comprise a computer program. The methods according to the disclosure can thereby be performed quickly, reproducibly and robustly. The individual computer program products are configured such that the method steps of the methods according to the disclosure can be performed by the computer. The computer must have the necessary specification such as, for example, a suitable RAM, a suitable graphics card or a suitable logic unit, in order to be able to perform the respective method steps efficiently. The individual computer program products are stored, for example, on a computer-readable medium or on a network or server, from where they can be loaded into the processor of a local computer, which processor may be connected directly to the medical imaging apparatus, in particular a magnetic resonance apparatus, or may be embodied as a part. In addition, control data of the individual computer program products can be stored on an electronically readable data storage medium. The control data in the electronically readable data storage medium can be embodied such that it performs at least one of the methods according to the disclosure when the data storage medium is used in a computer. Thus the individual computer program products can also constitute the electronically readable data storage medium. Examples of electronically readable data storage media are a DVD, a magnetic tape, a hard disk or a USB stick, on which is stored electronically readable control data, in particular software (see above). When this control data (software) is read from the data storage medium and stored in a controller and/or computer, all the embodiments according to the disclosure of the above-described methods can be performed. Hence the disclosure can also proceed from said computer-readable medium and/or from said electronically readable data storage medium.

In addition, the disclosure is based on a computer-readable data storage medium, which comprises a program that is intended to perform a method for automatically positioning a region of interest of a patient for a medical imaging examination in an isocenter of a medical imaging apparatus.

In addition, the disclosure can also comprise a computer-readable data storage medium, which comprises a program that is intended to perform a method for identifying a region of interest of a patient in a position-determination image.

FIG. 1 shows schematically a medical imaging apparatus 10. In the present exemplary embodiment, the medical imaging apparatus 10 is formed by a magnetic resonance apparatus 11, and the present disclosure is explained with reference to the magnetic resonance apparatus 10 by way of example. The present disclosure is not limited, however, to the embodiment of the medical imaging apparatus 10 as a magnetic resonance apparatus 11, and other embodiments of the medical imaging apparatus 10, for instance a computed tomography apparatus, a PET apparatus, etc. are always conceivable.

The magnetic resonance apparatus 11 comprises a scanner 12 formed by a magnet. The magnetic resonance apparatus 11 also comprises a patient receiving region 13 for accommodating a patient 14. In the present exemplary embodiment, the patient receiving region 13 is shaped as a cylinder and is enclosed in a circumferential direction cylindrically by the scanner 12, in particular by the magnet. In principle, however, it is always conceivable that the patient receiving region 13 has a different design. The patient 14 can be moved and/or shifted into the patient receiving region 13 by a patient positioning apparatus 15 of the magnetic resonance apparatus 11. The patient positioning apparatus 15 comprises for this purpose a patient couch 16, which is configured to be able to move inside the patient receiving region 13. In particular, said patient table 16 is mounted such that it can move in the direction of a longitudinal extent of the patient receiving region 13 and/or in the z-direction.

The scanner 12, in particular the magnet unit, comprises a superconducting main magnet 17 for generating a powerful and in particular constant main magnetic field 18. The scanner 12, in particular the magnet unit, further comprises a gradient coil 19 for generating magnetic field gradients, which are used for spatial encoding during imaging. The gradient coil 19 is controlled by a gradient controller 20 of the magnetic resonance apparatus 11. The scanner 12, in particular the magnet unit, further comprises a radiofrequency (RF) antenna 21 for exciting a polarization, which establishes itself in the main magnetic field 18 generated by the main magnet 17. The radiofrequency antenna 21 is controlled by a radiofrequency antenna controller 22 of the magnetic resonance apparatus 11 and radiates high-frequency magnetic resonance sequences into the patient receiving region 13 of the magnetic resonance apparatus 11. In an exemplary embodiment, the scanner 12 and/or one or more components of the scanner 12 (e.g. gradient coil 19, gradient controller 20, RF antenna 21, RF antenna controller 22) includes processor circuitry that is configured to perform one or more functions and/or operations of the scanner 12 (or components therein).

The magnetic resonance apparatus 11 comprises a system controller 23 for controlling the main magnet 17, the gradient controller 20 and the radiofrequency antenna controller 22. The system controller 23 centrally controls the magnetic resonance apparatus, for instance the implementation of a predetermined imaging gradient echo sequence. In addition, the system controller 23 comprises an analyzer (not presented in further detail) for analyzing medical image data acquired during the magnetic resonance examination. In an exemplary embodiment, the system controller 23 includes processor circuitry that is configured to perform one or more functions and/or operations of the system controller 23.

In addition, the magnetic resonance apparatus 11 comprises a user interface 24, which is connected to the system controller 23. Control data such as imaging parameters, for instance, and reconstructed magnetic resonance images can be displayed for a medical operator on an output 25, for example on at least one monitor, of the user interface 24. In addition, the user interface 24 comprises an input 26, which can be used by the medical operator to enter information and/or parameters during a measurement process.

The magnetic resonance apparatus 11 also comprises a computer 29 for performing a method according to the disclosure for automatically positioning a region of interest of a patient 14 for a medical imaging examination, in particular a magnetic resonance examination, in an isocenter 31 of the medical imaging apparatus 10, in particular of the magnetic resonance apparatus 11. For the purpose of performing the method for automatic positioning of a region of interest of a patient 14 for a medical imaging examination in the isocenter 31 of the magnetic resonance apparatus 11, the computer 29 comprises necessary software and/or computer programs, for instance positioning software and/or positioning programs, which are stored in a memory unit (not presented in greater detail) of the computer 19. The software and/or computer programs are configured to perform the method according to the disclosure for automatically positioning a region of interest of a patient 29 for a medical imaging examination in an isocenter of 31 of a medical imaging apparatus 10, in particular of the magnetic resonance apparatus 11, on execution of the software and/or computer programs by a processor of the computer 29. In particular, the computer 29 is configured to perform the method according to the disclosure for automatically positioning a region of interest of a patient 14 for a medical imaging examination in an isocenter of a medical imaging apparatus 10, in particular of the magnetic resonance apparatus 11, automatically and/or autonomously using the software and/or computer programs. In an exemplary embodiment, the computer 29 includes processor circuitry that is configured to perform one or more functions and/or operations of the computer 29.

The medical imaging apparatus 10 shown, in particular the magnetic resonance apparatus 11 shown, can obviously include further components typically present in medical imaging apparatuses 10, in particular in the magnetic resonance apparatuses 11. Furthermore, since a person skilled in the art knows how a medical imaging apparatus 10, in particular the magnetic resonance apparatus 11, works in general, a detailed description of the further components is not given.

FIG. 2 shows schematically a procedure of the method according to the disclosure for automatically positioning a region of interest of a patient 14 for a medical imaging examination. At the start of the method, the patient 14 is already in position on the patient table 16 of the patient positioning apparatus 15. In addition, where required, all add-on units required for the forthcoming medical imaging examination, in particular magnetic resonance examination, are located and/or are in position on the patient 14 and/or on the patient table 16. Such an add-on unit may comprise, for instance, a local radiofrequency antenna 32, which is arranged around a region of interest of the patient 14 in order to capture in particular magnetic resonance signals.

In a first method step 100, the region of interest of the patient 14 is brought into the patient receiving region 13 of the medical imaging apparatus 10, in particular of the magnetic resonance apparatus 11, for a position-determination measurement. In this process, the patient table 16 of the patient positioning apparatus 15 is preferably brought, in particular moved, into the patient receiving region 13 such that the region of interest of the patient 14 lies within the patient receiving region 13. Said bringing and/or moving of the patient table 16 into the patient receiving region 13 is controlled by the computer 29, in particular controlled automatically and/or autonomously by the computer 29.

In this first method step 100, the patient table 16 is thus positioned within the patient receiving region 13 until the region of interest of the patient 14 lies and/or is in position within a field of view (FOV) 33 of the medical imaging apparatus 10, in particular of the magnetic resonance apparatus 11.

Spatial information for the patient 14 on the patient table 16 of the patient positioning apparatus 15 is used for bringing the region of interest of the patient 14 into the patient receiving region 13 in this first method step 100. Said spatial information can be provided to the computer 29. Said spatial information can be provided to the computer 29 by means of registration data of the patient 14. The registration data of the patient 14 is preferably captured earlier in time than the medical imaging examination, in particular the magnetic resonance examination, and saved in a registrator (not presented in further detail), which registrator is connected to the computer 29 for the purpose of data transfer. The registration information can comprise, for instance, a position and/or orientation of the patient 14 on the patient table 13. Alternatively or additionally, the registration information can also comprise examination information on the patient 14, which examination information on the patient 14 includes, for instance, an examination region of the patient 14. By means of this registration information, the computer 29 can determine and/or assess automatically and/or autonomously a position of a region of interest of the patient 14 with respect to the patient table 16, and, when the patient table 16 is subsequently brought into the patient receiving region 13, the patient table 16 can be positioned such that the determined and/or assessed region of interest of the patient 14 lies in the FOV 33 of the medical imaging apparatus 10, in particular of the magnetic resonance apparatus 11.

Alternatively or additionally, the spatial information can be provided to the computer 29 also by means of a marking unit (marker) 27. The marking unit 27 may comprise, for example, an optical marking unit 27, for instance an optical laser marking unit. The marking unit 27 is preferably comprised by the medical imaging apparatus 10, in particular the magnetic resonance apparatus 11, and arranged outside the patient receiving region 13. For example, the marking unit 27, in particular the optical laser marking unit, can project an optical marker, for instance a cross, on the patient 14. In this case, the patient 14, or the patient table 16, is thus preferably moved until a position of the region of interest of the patient 14 coincides with a position of the projected marker, for instance with the projected cross. Since a distance of the marking unit 27 from an FOV 33 and/or isocenter 31 of the medical imaging apparatus 10, in particular of the magnetic resonance apparatus 11, is predefined in the case of a permanently installed marking unit 27 inside the medical imaging apparatus 10, in particular the magnetic resonance apparatus 11, it is possible for the computer 29, when the patient table 16 is subsequently brought into the patient receiving region 13, to use this spatial information to position the patient table 16 automatically and/or autonomously such that the region of interest of the patient 14 lies in the FOV 33 of the medical imaging apparatus 10, in particular of the magnetic resonance apparatus 11. In an exemplary embodiment, the marking unit (marker) 27 includes processor circuitry that is configured to perform one or more functions and/or operations of the marking unit 27.

Alternatively or additionally, the spatial information can be provided to the computer 29 also by means of camera data from a camera 28. The camera 28 is preferably comprised by the medical imaging apparatus 10, in particular the magnetic resonance apparatus 11. The camera 28 is preferably arranged on a wall and/or a ceiling of an examination room in which the medical imaging apparatus 10, in particular the magnetic resonance apparatus 11, is located. In addition, the camera 28 comprises a 2D camera and/or a 3D camera, so that 2D camera data and/or 3D camera data can be provided to the computer 29 as the spatial information. The computer 29 can use the provided camera data to ascertain and/or determine automatically and/or autonomously a surface image of the patient 14. The computer 29 can automatically and/or autonomously use the surface image to perform a segmentation into individual regions, in particular into individual body regions, of the patient 14. In addition, the computer 29 can automatically and/or autonomously determine and/or assess for the individual segmented regions, in particular the individual segmented body regions, a position with respect to the patient table 16. The computer 29 can automatically and/or autonomously associate the region of interest of the patient 14 with one of these segmented regions, in particular one of these segmented body regions. When the patient table 16 is subsequently brought into the patient receiving region 13, the computer 29 can automatically and/or autonomously position the patient table 16 such that the segmented region comprising the region of interest of the patient 14 lies in the FOV 33 of the medical imaging apparatus 10, in particular of the magnetic resonance apparatus 11.

In a second method step 101, which follows the first method step 100, the position-determination measurement is carried out, and position-determination image data is captured by means of the medical imaging apparatus 10, in particular the magnetic resonance apparatus 11. The position-determination image data is captured by means of the position-determination measurement. The position-determination measurement is performed automatically and/or autonomously under the control of the computer 29. For the position-determination measurement, the computer 29 sets measurement parameters such that an extended and/or maximum FOV 33 is available in the position-determination measurement. An extended and/or maximum FOV 33 also encompasses edge regions of a capture region within the patient receiving region 13 of the medical imaging apparatus 10, in particular of the magnetic resonance apparatus 11, in which edge regions of the capture region the physical image capture conditions are no longer ideal. Although this can lead to distortions in the captured image data, in particular in the position-determination image data, this is adequate for determining the position of the region of interest of the patient 14 with respect to the isocenter 31 of the medical imaging apparatus 10, in particular of the magnetic resonance apparatus 11.

Particularly advantageously, the extended and/or maximum FOV 33 encompasses a region that is at least 1.2 times larger than an FOV 33 for a clinical and/or diagnostic imaging measurement. Particularly advantageously, the extended and/or maximum FOV 33 encompasses a region that is at least 1.3 times larger than an FOV 33 for a clinical and/or diagnostic imaging measurement. Particularly advantageously, the extended and/or maximum FOV 33 encompasses a region that is at least 1.4 times larger than an FOV 33 for a clinical and/or diagnostic imaging measurement. Particularly advantageously, the extended and/or maximum FOV 33 encompasses a region that is at least 1.5 times larger than an FOV 33 for a clinical and/or diagnostic imaging measurement.

In this second method step 101, the position-determination measurement is carried out at a smaller and/or lower resolution than a resolution of a diagnostic and/or medical imaging measurement, in particular a magnetic resonance measurement. For this purpose, the computer 29 automatically and/or autonomously sets the measurement parameters accordingly before the position-determination measurement. The position-determination measurement can be performed particularly quickly because of the smaller and/or lower resolution of the position-determination measurement. The position-determination measurement takes preferably at most 10 s in this second method step 101. Particularly advantageously, the position-determination measurement takes at most 8 s to perform. Particularly advantageously, the position-determination measurement takes at most 6 s to perform. Particularly advantageously, the position-determination measurement takes at most 5 s to perform. Particularly advantageously, the position-determination measurement takes at most 4 s to perform. Particularly advantageously, the position-determination measurement takes at most 3 s to perform.

In a third method step 102, which follows the second method step 101, the computer 29 automatically and/or autonomously performs an analysis of the position-determination image data captured in the second method step 101. The computer 29 determines automatically and/or autonomously from the position-determination image data the region of interest of the patient 14 in the position-determination image data. For this purpose, the computer 29 automatically and/or autonomously creates a position-determination image, and identifies automatically and/or autonomously the region of interest of the patient 14 in the position-determination image.

For the purpose of identifying the region of interest of the patient 14 in the position-determination image, in the third method step 102, a computer-implemented method, in particular a machine learning method, is started in order to identify the region of interest of the patient 14 in the position-determination image. FIG. 3 shows in greater detail this computer-implemented method for identifying the region of interest of the patient 14 in the position-determination image. This computer-implemented method for identifying the region of interest of the patient 14 in the position-determination image is performed by a provider system 30. In the present exemplary embodiment, the computer 29 comprises the provider system 30. In an alternative embodiment, the provider system 30 can also be embodied separately from the computer 29, and connected to the computer 29 via a data transfer unit. The provider system 30 preferably comprises a dedicated processor and/or computer, which is not presented in further detail. In addition, the provider system 30 comprises an interface (not presented in further detail), by means of which interface the input data, in particular the position-determination image, can be provided.

In a first sub-step 102.1 of the computer-implemented method for identifying the region of interest of the patient 14 in the position-determination image, first the position-determination image is provided, wherein the position-determination image preferably comprises the region of interest of the patient 14, and/or the region of interest of the patient 14 is shown in the position-determination image (FIG. 3).

In a second sub-step 102.2, a resultant image EB is determined by applying a trained function TF to input data comprising the position-determination image, wherein the resultant image EB comprises an identification of the region of interest of the patient 14 (FIG. 3). The trained function TF is stored in the provider system 30 or is provided in the provider system 30 for the computer-implemented method for identifying the region of interest of the patient 14 in a position-determination image.

In a subsequent, third sub-step 102.3, the resultant image EB is then provided (FIG. 3). The resultant image EB here comprises in particular the position-determination image comprising an identified region of interest of the patient 14. For example, the identified region of interest of the patient 14 can be indicated in the position-determination image. The resultant image EB is preferably provided by means of the provider system 30, in particular the interface of the provider system 30. The resultant image EB is provided in this case by the provider system 30 of the computer 29 for positioning the region of interest of the patient 14 in the isocenter 31 of the medical imaging apparatus 10, in particular of the magnetic resonance apparatus 11.

Identifying the region of interest of the patient 14 within the position-determination image can be based here in particular on a machine learning method, also known as a deep learning method, which is based on the artificial neural network, in particular the trained function TF. An artificial neural network (ANN), in particular the trained function TF, is in particular a network of artificial neurons that is modeled in a computer program. The artificial neural network, in particular the trained function TF, is typically based on an interconnection of a plurality of artificial neurons. The artificial neurons are typically arranged in different layers. Usually the artificial neural network, in particular the trained function TF, comprises an input layer and an output layer, the neuron output of which is the only part of the artificial neural network, in particular of the trained function TF, to be visible. Layers lying between the input layer and the output layer are typically referred to as hidden layers. It is typical for an architecture and/or topology of an artificial neural network, in particular of the trained function TF, first to be initiated, and then to be trained in a training phase for a specific task or for a plurality of tasks in a training phase. Said training of the artificial neural network, in particular of the trained function TF, typically comprises changing a weight of a connection between two artificial neurons of the artificial neural network, in particular of the trained function TF. The training of the artificial neural network, in particular of the trained function TF, can also comprise developing new connections between artificial neurons, removing existing connections between artificial neurons, adjusting threshold values of the artificial neurons and/or adding or removing artificial neurons.

Figure 4:
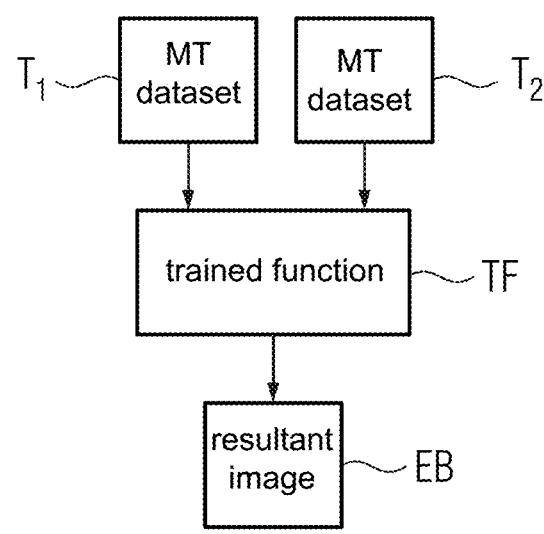
FIG. 4 shows a process of providing a trained function according to an exemplary embodiment.

The artificial neural network, in particular the trained function TF, in particular has already been trained in advance suitably for identifying the region of interest of the patient 14 in the position-determination image. For said training of the artificial neural network, in particular of the trained function TF, training image datasets T1, T2 in particular are used in which, for example, in a position-determination image, a region of interest of the patient 14 is already associated with examination information and/or anatomy information of the patient 14 (FIG. 4). The medical training datasets T1, T2 are acquired in this case typically from training people and/or training patients who are different from the patient 14.

The trained function TF can be based on at least one training image dataset T1, T2 containing training data, wherein the training data comprises a position-determination image comprising a characteristic shape of the region of interest, which characteristic shape is associated with the region of interest of the patient 14. For instance, if the region of interest of the patient 14 comprises an organ, the associated characteristic shape can comprise the shape of the organ, for instance a shape of a liver and/or a shape of a heart. In addition, the associated characteristic shape can include also a shape of a bone and/or of blood vessels etc. lying within the region of interest of a patient 14.

Alternatively or additionally, the trained function TF can also be based on at least one training image dataset T1, T2 containing training data, wherein the training data comprises a position-determination image comprising landmark recognition of the region of interest of a patient 14, which landmark recognition is associated with the region of interest. Landmarks preferably include typical points in an image that can be associated exactly with a specific organ and/or a specific joint and/or a specific body region. On the basis of said recognition, a trained function TF can advantageously be provided for rapid identification of a region of interest of a patient 14 in a position-determination image.

Alternatively or additionally, the trained function RF can also be based on at least one training image dataset T1, T2 containing training data, wherein the training data comprises a position-determination image comprising segmentation into organ structures and/or body structures of the region of interest, which segmentation is associated with said region of interest of a patient 14.

Said position-determination image preferably comprises a 2D position-determination image. In addition in this case, the training data of the at least one training image dataset T1, T2 of the trained function likewise comprises 2D image data in order to attain rapid identification and analysis of the region of interest of the patient 14.

In the third method step 102, after the identification of the region of interest of the patient 14, a position of the region of interest of the patient 14 is also determined. In this process, the computer 29 automatically and/or autonomously determines the position of the region of interest of the patient 14 with respect to the isocenter 31 of the medical imaging apparatus 10, in particular of the magnetic resonance apparatus 11. In particular, the computer 29 can here determine a distance of the region of interest of the patient 14 with respect to the isocenter 31 of the medical imaging apparatus 10, in particular of the magnetic resonance apparatus 11. In this process, the computer 29 preferably determines the position of the region of interest of the patient 14 with respect to the isocenter 31 of the medical imaging apparatus 10, in particular of the magnetic resonance apparatus 10, on the basis of the resultant image EB provided in the computer-implemented method for identifying the region of interest of the patient 14.

Automatic positioning of the patient 14 is performed in a fourth method step 103, which follows the third method step 102 of analyzing the position-determination image data. In this process, the automatic positioning of the patient 14 is performed such that after the positioning of the patient 14, the position of the region of interest of the patient 14 coincides with the position of the isocenter 31 of the medical imaging apparatus 10, in particular of the magnetic resonance apparatus 11. The automatic and/or autonomous positioning of the region of interest of the patient 14 here includes automatically moving the patient table 16 until the region of interest of the patient 14 coincides with the isocenter 31 of the medical imaging apparatus 10, in particular of the magnetic resonance apparatus 11. The patient table 16 is controlled in this case automatically by the computer 29 for moving the patient table 16.

In a further method step 104, in particular a fifth method step 104, which comprises a planning step, a planning measurement is performed automatically by the medical imaging apparatus 10, in particular by the magnetic resonance apparatus 11. The planning measurement is used to capture planning measurement data for planning the medical imaging examination, in particular the magnetic resonance examination, on the region of interest of the patient 14. By automatically positioning the region of interest of the patient 14 in the isocenter 31 of the medical imaging apparatus 11, in particular of the magnetic resonance apparatus 11, the region of interest of the patient 14 is thus in an optimum position within the patient receiving region 13, in particular in the isocenter 31, for the planning measurement and also for a subsequent medical imaging examination, in particular a magnetic resonance examination.

In this fifth method step 104, the planning measurement is carried out at a smaller and/or lower resolution than a resolution of a diagnostic and/or medical imaging measurement, in particular a magnetic resonance measurement. For this purpose, the computer 29 automatically and/or autonomously sets the measurement parameters accordingly before the planning measurement. The planning measurement can be performed particularly quickly because of the smaller and/or lower resolution of the planning measurement.

In this fifth method step, the computer 29 automatically generates and/or creates a planning image from the planning measurement data of the planning measurement, wherein the planning image comprises a magnified representation of the region of interest of the patient 14. In particular, the region of interest of the patient 14 is presented in a zoom-view in the planning image.

A user, in particular the medical operator, and/or a planning processor can then use the planning image, in particular the magnified representation of a segment containing the region of interest of the patient 14, to plan the medical imaging examination. Said planning processor can be comprised by the computer 29 or else can be embodied separately from the computer. In particular, a user, in particular the medical operator, and/or a planning processor can thus use the planning image to set and/or specify, on the basis of the planning image, individual examination parameters for the forthcoming medical imaging examination. For example, a user, in particular the medical operator, and/or a planning processor can thus use the planning image to determine and/or set for a magnetic resonance examination a slice thickness and/or a slice position and/or an orientation of a slice and/or a number of slices to be captured, etc.

In addition in this fifth method step 104, while the planning image is being provided and/or while the medical imaging examination, in particular the magnetic resonance examination, is being planned, at least one adjustment measurement can be performed for the forthcoming medical imaging examination, in particular the magnetic resonance examination.

Moreover in this fifth method step 104, the computer 29 can automatically and/or autonomously check planning data after the planning of the medical imaging examination, in particular of the magnetic resonance examination, has been carried out. In addition, the computer 29 can automatically generate output information on the basis of the check, and output said output information to the user, in particular to the medical operator, by means of the user interface 24, in particular by means of the output 25 of the user interface 24. Preferably, once planning of the medical imaging examination, in particular of the magnetic resonance examination, on the basis of the planning image is complete, the medical imaging examination, in particular the magnetic resonance examination, is carried out on the region of interest of the patient 14 using the measurement parameters set in the fifth method step.

If the medical imaging examination involves a magnetic resonance examination, it can also be provided in this method for automatically positioning the region of interest of the patient 14 for a magnetic resonance examination in an isocenter 31 of the magnetic resonance apparatus 11, that in a further, in particular optional, sixth method step 105, information on a radiofrequency antenna 32 is determined for the planned magnetic resonance examination from the position-determination image data. The radiofrequency antenna 32 comprises in this case a local radiofrequency antenna 32, which is arranged around the region of interest of the patient 14 for capturing magnetic resonance image data.

The captured information on the radiofrequency antenna 32 may comprise a type of the radiofrequency antenna 32 and/or a position of the radiofrequency antenna 32 and/or an orientation of the radiofrequency antenna 32. In addition in this sixth method step 105, the computer 29 automatically compares the captured information on the radiofrequency antenna 32 with examination information and/or patient registration information and/or a reference position for the radiofrequency antenna 32. The computer 29 can thereby check whether the correct local radiofrequency antenna 32 is being used for the forthcoming magnetic resonance examination. In addition, the computer 29 can check in this sixth method step 105 whether the local radiofrequency antenna 32 arranged around the region of interest of the patient 14 is in the correct position. In this process, output information can be generated for the user as a function of the comparison of the captured information on the radiofrequency antenna 32 with the examination information and/or the patient registration information and/or the reference position of the radiofrequency antenna 32, and this output information can be output to the user by means of the user interface 24, in particular by means of the output 25 of the user interface 34.

Although the disclosure has been illustrated and described in detail using the preferred exemplary embodiment, the disclosure is not limited by the disclosed examples, and a person skilled in the art can derive other variations therefrom without departing from the scope of protection of the disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for automatically positioning a region of interest of a patient for a magnetic resonance (MR) examination in an isocenter of a MR imaging apparatus, the method comprising:
   moving the region of interest of the patient into a patient receiving region of the medical imaging apparatus to facilitate a position-determination measurement;
   performing the position-determination measurement to capture position-determination image data;
   determining, based on the position-determination image data, information of a local radiofrequency antenna configured to capture MR signals from the patient during the MR examination;
   determining a position of the region of interest of the patient based on the position-determination image data and the information of the radiofrequency antenna; and
   automatically positioning the patient such that the position of the region of interest of the patient coincides with a position of the isocenter of the MR imaging apparatus.

2. The method as claimed in claim 1, wherein moving the region of interest of the patient into the patient receiving region comprises positioning the region of interest of the patient within a field of view (FOV) of the MR imaging apparatus.

3. The method as claimed in claim 1, wherein performance of the position-determination measurement uses a first field of view (FOV) of the MR imaging apparatus having a first FOV size, and the MR examination uses a second FOV having a second FOV size that is smaller than the first FOV size.

4. The method as claimed in claim 1, wherein the region of interest of the patient is brought into the patient receiving region with aid of a marker.

5. The method as claimed in claim 1, wherein the region of interest of the patient is brought into the patient receiving region based on registration data of the patient.

6. The method as claimed in claim 1, wherein the region of interest of the patient is brought into the patient receiving region based on camera data from a camera.

7. The method as claimed in claim 6, further comprising:
determining a surface image of the patient based on the camera data of the camera, and
segmenting the patient into individual regions based on the surface image of the patient.

8. The method as claimed in claim 1, wherein the position-determination measurement takes at most 10 seconds to perform.

9. The method as claimed in claim 1, further comprising creating a position-determination image based on the analysis of the position-determination image data, wherein the region of interest of the patient is identified automatically in the position-determination image.

10. The method as claimed in claim 9, further comprising performing a computer-implemented method to identify the region of interest of the patient in the position-determination image, the computer-implemented method including:
providing the position-determination image that includes the region of interest of the patient;
applying a trained function to input data including the position-determination image to determine a resultant image including an identification of the region of interest; and
providing the resultant image as an output.

11. The method as claimed in claim 1, wherein the automatic positioning of the region of interest of the patient comprises moving a patient table automatically.

12. The method as claimed in claim 1, wherein the determined information on the local radiofrequency antenna includes: a type of the local radiofrequency antenna, a position of the local radiofrequency antenna, and/or an orientation of the local radiofrequency antenna.

13. The method as claimed in claim 1, further comprising:
comparing the determined information of the local radiofrequency antenna with: examination information, patient registration information, and/or a reference position for the local radiofrequency antenna; and
determining a deviation of a position of the local radiofrequency antenna from the reference position for the local radiofrequency antenna based on the comparison.

14. The method as claimed in claim 13, further comprising generating and outputting output information as a function of the comparison of the captured information on the local radiofrequency antenna with the examination information, the patient registration information, and/or the reference position of the local radiofrequency antenna.

15. The method as claimed in claim 1, further comprising:
performing, after the automatic positioning of the patient, a planning measurement to facilitate planning of the MR imaging examination on the region of interest of the patient, the planning measurement generating planning measurement data.

16. The method as claimed in claim 15, wherein at least one planning image is generated and/or created based on the planning measurement data of the planning measurement, the at least one planning image including a magnified representation of the region of interest of the patient.

17. The method as claimed in claim 16, performing at least one adjustment measurement for the MR imaging examination while the at least one planning image is being provided and/or while the MR imaging examination is being planned.

18. The method as claimed in claim 15, further comprising: after the planning of the MR imaging examination, automatically checking the planning measurement data, and generating output information based on the checking.

19. A non-transitory computer-readable storage medium with an executable program stored thereon, that when executed, instructs a processor to perform the method of claim 1.

20. A computer program product, embodied on a non-transitory computer-readable storage medium, having a computer program directly loadable into a memory of a programmable computer, when executed by the programmable computer, causes the MR imaging apparatus to perform the method as claimed in claim 1.

21. A medical imaging apparatus comprising:
a scanner;
a local radiofrequency antenna configured to capture magnetic resonance (MR) signals from patient during a MR examination of the patient;
a patient receiving region that is surrounded at least partially by the scanner;
a patient positioning apparatus including a patient table, the patient position apparatus being configured to move in a horizontal direction; and
a computer that is configured to perform the method as claimed in claim 1 to control the patient positioning apparatus to automatically position the region of interest of the patient in the isocenter of the medical imaging apparatus for the MR examination.

22. The method as claimed in claim 1, wherein the position-determination measurement is performed using a first field of view (FOV) of the MR imaging apparatus, the method further comprising:
reducing the first FOV to a second FOV smaller than the first FOV; and
performing the MR examination using the second FOV.

23. A computer-implemented method for identifying a region of interest of a patient in a position-determination image, comprising:
obtaining the position-determination image generated by a magnetic resonance (MR) imaging apparatus, the position-determination image including the region of interest of the patient, wherein the position-determination image is generated based on position-determination image data and information of a local radiofrequency antenna configured to capture MR signals from the patient during a MR examination of the patient performed by the MR imaging apparatus;
applying a trained function to input data including the position-determination image to determine a resultant image, wherein the resultant image includes an identification of the region of interest; and
providing the resultant image as an electronic output signal.

24. The method as claimed in claim 23, wherein the trained function is based on at least one training image dataset containing training data, the training data including the position-determination image that includes: examination information and/or anatomy information, and an associated region of interest.

25. The method as claimed in claim 23, wherein the trained function is based on at least one training image dataset containing training data, the training data including the position-determination image that includes a characteristic shape of the region of interest, the characteristic shape being associated with the region of interest.

26. The method as claimed in claim 23, wherein the trained function is based on at least one training image dataset containing training data, the training data including the position-determination image that includes landmark recognition in the region of interest, the landmark recognition being associated with the region of interest.

27. The method as claimed in claim 23, wherein the trained function is based on at least one training image dataset containing training data, the training data including the position-determination image that includes segmentations of organ structures and/or body structures of the region of interest, the segmentations being associated with the region of interest.

28. The method as claimed in claim 23, wherein the position-determination image comprises a two-dimensional (2D) position-determination image, the trained function being based on at least one training image dataset containing training data, and wherein the training data of the at least one training image dataset includes at least 2D training image data.

29. A provider system for providing a resultant image, comprising:
- an interface; and
- a computer that is configured to apply a trained function to input data including a position-determination image to determine the resultant image that includes an identification of a region of interest, the position-determination image being generated based on position-determination image data and information of a local radiofrequency antenna configured to capture magnetic resonance (MR) signals from a patient during a MR examination of the patient performed by a MR imaging apparatus,
- wherein the position determination image is provided by the interface and/or the computer, and wherein the interface is configured to provide the resultant image as an output of the provider system.

* * * * *